United States Patent
Mossi et al.

(10) Patent No.: US 7,057,058 B2
(45) Date of Patent: Jun. 6, 2006

(54) PROCESS FOR THE PREPARATION OF 13-CIS-RETINOIC ACID

(75) Inventors: Waldo Mossi, Biasca (CH); Patrizio Aspari, Biasca (CH); Enrico Braglia, Biasca (CH); Riccardo Braglia, Biasca (CH)

(73) Assignee: Helsinn Advanced Synthesis SA, Biasca (CH)

( * ) Notice: Subject to any disclaimer, the term of this patent is extended or adjusted under 35 U.S.C. 154(b) by 0 days.

(21) Appl. No.: 11/058,290

(22) Filed: Feb. 16, 2005

(65) Prior Publication Data

US 2005/0192351 A1    Sep. 1, 2005

(30) Foreign Application Priority Data

Feb. 17, 2004  (EP) ................... 04003491

(51) Int. Cl.
*C07C 51/00* (2006.01)
*C07C 51/353* (2006.01)

(52) U.S. Cl. ...................... 554/125; 554/124
(58) Field of Classification Search .............. None
See application file for complete search history.

(56) References Cited

U.S. PATENT DOCUMENTS 4,556,518 A * 12/1985 Lucci .................... 554/125

* cited by examiner

*Primary Examiner*—Paul A. Zucker
(74) *Attorney, Agent, or Firm*—Young & Thompson

(57) ABSTRACT

A process for the preparation of 13-cis-retinoic acid (I)

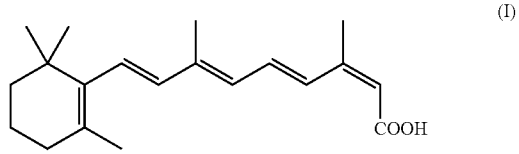

from 3-methyl-5-(2,6,6-trimethyl-1-cyclohexen-1-yl)-2,4-pentadienyl)-triphenylphosphonium chloride (IIa)

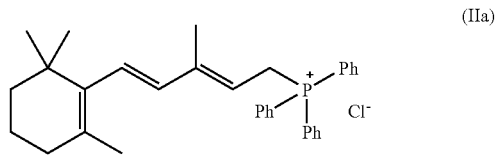

and 5-hydroxy-4-methyl-2(5H)-furanone (III)

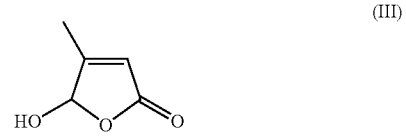

is herein disclosed. Compounds (IIa) and (III) are reacted in ethanol as the solvent and KOH as the base at a temperature ranging from −5 to 0° C. to give a mixture of retinoic acids which is isomerized to (I) by treatment with a palladium complex.

7 Claims, No Drawings

PROCESS FOR THE PREPARATION OF 13-CIS-RETINOIC ACID

FIELD OF THE INVENTION

The present invention relates to a process for the preparation of 13-cis-retinoic acid.

BACKGROUND OF THE INVENTION 13-cis-Retinoic acid (I) is a compound of widespread use in cosmetics, due to its anti-acne properties.

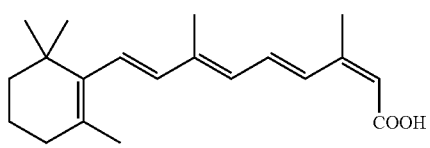

Among the available methods for its preparation, the one disclosed in EP 0111325 comprises the Wittig reaction between a salt of formula (II)

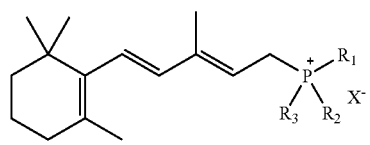

and 5-hydroxy-4-methyl-2(5H)-furanone (III)

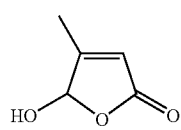

at temperatures ranging from −10 to −50° C. in a lower alcohol and in the presence of an alkali metal hydroxide, followed by isomerisation of the resulting mixture of 11,13-di-cis- and 13-cis-retinoic acid in the presence of a palladium, platinum or rhodium complex, the isomerisation occurring at a temperature ranging from 10 to 150° C., preferably from 40 to 65° C., more preferably from 45 to 55° C. 13-cis-retinoic acid can easily be isolated by cooling to a temperature preferably ranging from −15 to −10° C. and filtering the precipitate.

An improvement over this process is disclosed in EP 0644186 B1, which claims the preparation of (I) by reaction of salts of formula (II) and butenolide (III) in dimethylformamide as the solvent in the presence of lithium hydroxide, at a temperature ranging from −9 to +10° C., preferably from −5 to +5° C., even more preferably from −2 to +2° C. The resulting mixture of 11,13-di-cis and 13-cis-retinoic acid is subsequently isomerised, preferably by photochemical isomerisation at wavelengths from 200 to 600 nm. Even though this process allows to save energy costs, due to the fact that the Wittig reaction is carried out at a relatively high temperature, it still requires the use of dimethylformamide, whose use on industrial scale is undesirable, due to its toxicity and relatively high cost.

As a matter of fact, the whole procedure implies not only high costs but it is also cumbersome and can be only carried out in very large industrial plants.

Another process for the preparation of 13-cis-retinoic acid is disclosed in EP 959069, comprising the reaction of beta-ionone with a vinyl magnesium halide to give vinyl-beta-ionol, followed by the Wittig condensation of vinyl-beta-ionol with 4-hydroxy-3-methyl-butenolide to give a mixture of 13-cis-retinoic acid, 11-13-di-cis-retinoic acid and 11,13-di-trans-retinoic acid which is then subjected to photochemical isomerization.

The conversion of 11-cis, 13-cis-retinoic acid to 13-cis-retinoic acid is disclosed also in EP 850925. The photochemical isomerization requires of course a dedicated apparatus.

Also in this case the photochemical isomerization require the use of the irradiation technology, which, under the economical point of view, is not competitive with other technologies.

It would be therefore advantageous to provide a method for the preparation of 13-cis-retinoic acid which could allow both to save energy costs and avoid the use of toxic solvents.

DESCRIPTION OF THE INVENTION

It has now been found that highly pure 13-cis-retinoic acid can be obtained by carrying out the Wittig reaction in ethanol as the solvent and KOH as the base in a strictly controlled temperature range.

The present invention relates to a process for the preparation of 13-cis-retinoic acid (I)

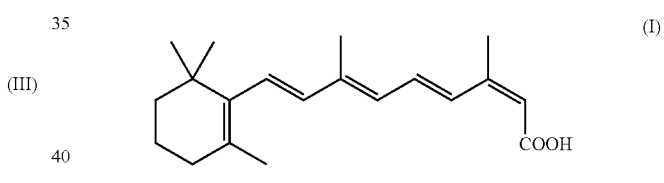

comprising:
a) reacting 3-methyl-5-(2,6,6-trimethyl-1-cyclohexen-1-yl)-2,4-pentadienyl)-triphenylphosphonium chloride (IIa)

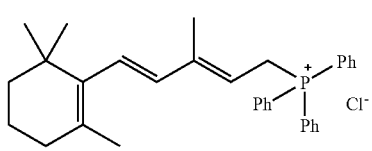

with 5-hydroxy-4-methyl-2(5H)-furanone (III)

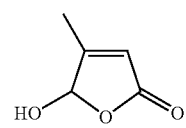

b) isomerising the product of step a) in an organic solvent and in the presence of a Pd(II) complex characterised in that step a) is carried out in ethanol or isopropyl alcohol as the solvent and KOH as the base, at a temperature ranging from −5 to 0° C.

For the isomerisation, the palladium compound is preferably Pd(NO₃)₂ and the solvent is preferably acetonitrile. The reaction is carried out at a temperature ranging from 45 to 55° C., preferably for no more than one hour in order to limit the formation of impurities, and the resulting 13-cis-retinoic acid is recovered by cooling to a temperature ranging from −5 to 0° C. Keeping the temperature within the range −5/0° C. (instead of within the range −15/−10° C., as disclosed in EP 0111325) allows to increase the quality of the product and save energy costs.

Compound (I) can be further purified by means of conventional methods. According to a preferred embodiment of the invention, compound (I) is hot-crystallised from ethanol or ethyl acetate; the product precipitates by cooling to a temperature ranging from −5 to 0° C.

Moreover the characteristics of the new synthesis process and in particular the higher reaction temperature make it suitable for use in any kind of industrial or laboratory plant. In fact, contrarily to the processes disclosed in the prior art (where in the key reaction step the salt of formula (II) and 5-Hydroxy-4-methyl-2(5H)-furanone)(III) react in a temperature range from −10° C. to −50° C.), it can be easily and cheaply reproduced in small- and medium-sized plants other than in large-sized plants.

The invention is now hereinafter illustrated in more detail by means of the following example.

EXAMPLE

Vinyl-β-ionol (39.5 g), absolute ethanol (120.5 g) and triphenylphosphine (42.8) are loaded into a 1 l reactor (R1) under nitrogen atmosphere, at an internal temperature of 20–25° C. 33% HCl (20.9 g) is slowly added and the mixture is stirred until complete dissolution. Once the reaction is complete C₅-butenolide (17.3 g) is added and the mixture is stirred at 20–25° C. for 15-30 min., cooled to −5–0° C. and added with a KOH ethanol solution (12.3% w/w, 173.4 g). Stirring is continued until completion of the reaction, thereafter the mixture is allowed to warm up to 20–25° C. and water (380 g) and hexane (137.0 g) are added under stirring. After 10–20 min., stirring is interrupted and the phases are separated. The aqueous phase is stored in a recipient R2, while the organic phase is added with methanol (12 g) and water (6.5 g) and the resulting mixture is stirred at 20–25° C. for 5–15° C. under nitrogen atmosphere. The organic phase is collected and stored in R1, while the aqueous phase is pooled with the one stored in R2, cooled to 0–10° C. under nitrogen atmosphere and added with a 85% phosphoric acid solution (about 20–22 g) adjusting the pH to 4–4.5. The resulting mixture is then added with ethyl acetate (72.4 g) and hexane (215 g), stirred at 20–25° C. under nitrogen atmosphere for 5–15 min. and filtered. The cake is washed with ethyl acetate (7.24 g) and hexane (21.5 g), and the filtrate is added to the organic phase stored in R1. The aqueous phase is separated, while the organic phase in R1 is extracted with 60.0 g of water. The aqueous phase is separated and pooled with the one stored, while the organic phase is extracted six times with methanol (34.0 g) and water (18.4 g). Each extraction is carried out under nitrogen atmosphere, stirring for 5–15 min. at 20–25° C. The methanol/water phases are pooled with the aqueous phase and back extracted five times with ethyl acetate (27.6 g) and hexane (82.0 g). Each extraction is carried out under nitrogen atmosphere stirring for 5–15 min. at 20–25° C. The organic phases are pooled with the one stored in R1 and concentrated to about 350 ml, distilling off the solvent under vacuum (250–300 mbar), keeping the internal temperature at 20–30° C. The residue is filtered collecting the filtrate in R2. The mixture contained in R2 is concentrated to about 60 ml, distilling off the solvent at 200 mbar keeping the internal temperature at 20–25° C. The residue is added with 21.3 g of ethyl acetate, warmed up to 50° C. and added with a solution of acetonitrile (1.65 g), Pd(NO₃)₂, triphenylphosphine (0.1015 g) and triethylamine (0.020 g). The mixture is kept under stirring at 50° C. under nitrogen atmosphere until completion of the reaction (1 h). The mixture is cooled down to −5–0° C. within two hours and stirred overnight, thereafter the precipitate is filtered and washed with 12.8 g of cold ethyl acetate. Yield: 18.0 g.

Crystallisation 13.0 g of (I) are loaded into R1, suspended in 133.5 g of absolute ethanol or ethyl acetate and refluxed at 75–80° C. until complete dissolution. The solution is filtered through celite/active charcoal and collected into R2 and the residue in R1 is taken up with hot ethanol (10.3 g), filtered and collected into R2. The filtrate is concentrated by distilling off at ambient pressure about 51.3 g of the solvent; residue is cooled to −5–0° C. and allowed to stand overnight.

The precipitate is filtered, washed with absolute ethanol (10.3 g) and dried under nitrogen (35° C., 50–100 mbar) to afford 9.00–11.00 g of pure (I).

What is claimed is:

1. A process for the preparation of 13-cis-retinoic acid (I)

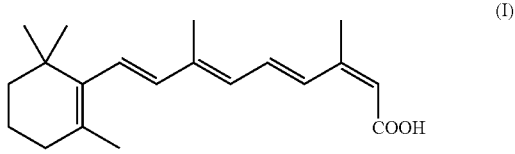

(I)

comprising:
a) reacting 3-methyl-5-(2,6,6-trimethyl-1-cyclohexen-1-yl)-2,4-pentadienyl)-triphenylphosphonium chloride (IIa)

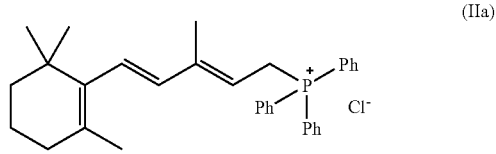

(IIa)

with 5-hydroxy-4-methyl-2(5H)-furanone (III)

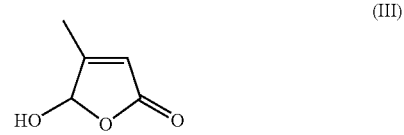

(III)

b) isomerising the product of step a) in an organic solvent and in the presence of Pd(II) complex characterised in that step a) is carried out in ethanol as the solvent and KOH as the base, at a temperature ranging from −5 to 0° C.

2. A process according to claim 1 wherein the Pd(II) compound is $Pd(NO_3)_2$.

3. A process according to claim 1 wherein the organic solvent used in step b) is acetonitrile.

4. A process according to claim 1 wherein, at the end of the isomerisation reaction, compound (I) is recovered by cooling to a temperature ranging from −5 to 0° C.

5. A process according to claim 2 wherein the organic solvent used in step b) is acetonitrile.

6. A process according to claim 2 wherein, at the end of the isomerisation reaction, compound (I) is recovered by cooling to a temperature ranging from −5 to 0° C.

7. A process according to claim 3 wherein, at the end of the isomerisation reaction, compound (I) is recovered by cooling to a temperature ranging from −5 to 0° C.

* * * * *